(12) United States Patent
Plancher et al.

(10) Patent No.: US 7,144,890 B2
(45) Date of Patent: Dec. 5, 2006

(54) SPIRO-PENTACYCLIC COMPOUNDS

(75) Inventors: Jean-Marc Plancher, Knoeringue (FR);
Sven Taylor, Riedisheim (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/042,884

(22) Filed: Jan. 25, 2005

(65) Prior Publication Data
US 2005/0165012 A1    Jul. 28, 2005

(30) Foreign Application Priority Data
Jan. 28, 2004 (EP) ................................. 04100304

(51) Int. Cl.
*A61K 31/44* (2006.01)
(52) U.S. Cl. ..................... 514/278; 514/232.5; 544/70; 544/153; 546/15; 546/197
(58) Field of Classification Search ................ 514/278, 514/232.5; 544/70, 153; 546/197, 15
See application file for complete search history.

(56) References Cited

U.S. PATENT DOCUMENTS

| 3,940,418 | A | 2/1976 | Hamilton |
| 5,462,960 | A | 10/1995 | Barth et al. |
| 5,596,106 | A | 1/1997 | Cullinan et al. |
| 5,624,941 | A | 4/1997 | Barth et al. |
| 6,355,631 | B1 | 3/2002 | Achard et al. |
| 6,479,479 | B1 | 11/2002 | Achard et al. |
| 6,518,264 | B1 | 2/2003 | Achard et al. |
| 6,566,356 | B1 | 5/2003 | Achard et al. |
| 6,734,176 | B1 | 5/2004 | Achard et al. |
| 2001/0027193 | A1 | 10/2001 | Achard et al. |
| 2002/0019383 | A1 | 2/2002 | Achard et al. |
| 2002/0035102 | A1 | 3/2002 | Achard et al. |
| 2003/0055033 | A1 | 3/2003 | Achard et al. |
| 2003/0119810 | A1 | 6/2003 | Achard et al. |
| 2003/0162808 | A1 | 8/2003 | Achard et al. |
| 2004/0157823 | A1 | 8/2004 | Achard et al. |
| 2004/0235816 | A1 | 11/2004 | Achard et al. |

FOREIGN PATENT DOCUMENTS

| EP | 565354 | 10/1993 |
| EP | 576357 | 12/1993 |
| EP | 658546 | 5/2001 |
| FR | 2783246 A1 | 3/2000 |
| FR | 2805810 A1 | 9/2001 |
| FR | 2805817 A1 | 9/2001 |
| FR | 2805818 A1 | 9/2001 |
| WO | WO9602248 | 2/1996 |
| WO | WO9719063 | 5/1997 |
| WO | WO0015609 | 3/2000 |
| WO | WO0046209 | 8/2000 |
| WO | WO0132663 | 5/2001 |
| WO | WO0164632 | 9/2001 |
| WO | WO0164633 | 9/2001 |
| WO | WO0164634 | 9/2001 |
| WO | WO0170700 | 9/2001 |
| WO | WO0228346 | 4/2002 |
| WO | WO02076949 | 10/2002 |
| WO | WO03020217 | 3/2003 |
| WO | WO0335005 | 5/2003 |
| WO | WO0337332 | 5/2003 |
| WO | WO03040107 | 5/2003 |
| WO | WO03051850 | 6/2003 |
| WO | WO03063781 | 8/2003 |
| WO | WO03077847 | 9/2003 |
| WO | WO03078413 | 9/2003 |
| WO | WO03082190 | 10/2003 |
| WO | WO03082833 | 10/2003 |
| WO | WO03084930 | 10/2003 |
| WO | WO03084943 | 10/2003 |
| WO | WO03086288 | 10/2003 |
| WO | WO03087037 | 10/2003 |
| WO | WO 2004/013120 A1 | 2/2004 |

OTHER PUBLICATIONS

D. Shire, et. al., J. Biol. Chem. 270 (8) (1995) 3726-31.
S. Munro, et. al., Nature 365 (1993) 61-61.
Y. Gaoni, et. al., J. Am. Chem. Soc., 86 (1964) 1646.
R. Mechoulam (Ed) "Cannabinoids as Therapeutic Agents" (1986) 1-20, CRC Press.

(Continued)

*Primary Examiner*—Amelia A. Owens
(74) *Attorney, Agent, or Firm*—George W. Johnston; Dennis P. Tramaloni

(57) ABSTRACT

The present invention relates to compounds of the formula (I)

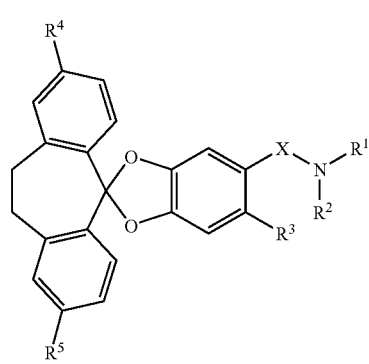

and pharmaceutically acceptable salts thereof, for use as therapeutically active substances. The compounds are useful for the treatment and/or prophylaxis of diseases which are associated with the modulation of CB1 receptors including obesity.

17 Claims, No Drawings

OTHER PUBLICATIONS

R.G. Pertwee, Pharmaceut. Sci. 3 (11) (1997) 539-545.
E.M. Williamson, et. al., Drugs 60 (6) (2000) 1303-1314.
R.G. Pertwee, Curr Med Chem, 6 (8) (1999) 635-664.
W.A. Devane, et. al., Science 258 (1992) 1946-9.
V. Di Marzo, et. al., Trends in Neuroscience 21 (12) (1998) 521-528.
A.C. Porter, et. al., Pharmacol. Ther., 90 (1) (2001) 45-60.
C.M. Williams, Psychopharmacology 143 (3) (1999) 315-317.
C.C. Felder, et. al., Proc. Natl. Acad. Sci. USA 90 (16) (1993) 7656-60.
G. Colombo, et. al., Life Sci. 63 (8) (1998) L113-PL117.
V. Di Marzo, et. al., Nature 410 (6830) 822-825.
F. Barth, et. al., "Cannabinoid Antagonists:From research tools to potential new drugs", Abstracts of Papers, 222nd ACS National Meeting, Chicago, IL Aug. 26-30, 2001.
AAI; M. Pacheco, et. al., J. Pharmacol. Exp. Ther. 257 (1) (1991) 170-183.
WIN54661; F. M. Casiano, et. al., NIDA Res. Monogr. 105 (1991) 295-6.
AM630; K. Hosohata, et. al., Life Sci. 61 (1997) 115-118.
R. Pertwee, et. al., Life Sci. 56 (23-24) (1995) 1949-55.
LY320135, C.C.Felder, et. al., J. Pharmacol Exp Ther 284 (1) (1998) 291-7.
M. Kanyonyo, et. al., Bioorg. Med. Chem. Lett 9 (15) (1999) 2233-2236.
F. Ooms, et. al., J. Med. Chem 45 (9) (2002) 1748-1756.
J.M. Mussinu, et. al., Bioorg Med Chem (2003) 11, 251.
S. Ruiu, et. al., J. Pharm. Expt. Ther. (2003) 306, 363.
G. Tarzia, et. al., Bioorg. Med. Chem. (2003), 11, 3965.

SPIRO-PENTACYCLIC COMPOUNDS

BACKGROUND OF THE INVENTION

Two different subtypes of cannabinoid receptors (CB1 and CB2) have been isolated and both belong to the G protein coupled receptor superfamily. An alternative spliced form of CB1, CB1A, has also been described, but it did not exhibit different properties in terms of ligand binding and receptor activation than CB1 (D. Shire, C. Carrillon, M. Kaghad, B. Calandra, M. Rinaldi-Carmona, G. Le Fur, D. Caput, P. Ferrara, J. Biol. Chem. 270 (8) (1995) 3726–31). The CB1 receptor is mainly located in the brain, whereas the CB2 receptor is predominately distributed in the periphery and primarily localized in spleen and cells of the immune system (S. Munro, K. L. Thomas, M. Abu-Shaar, Nature 365 (1993) 61–61). Therefore in order to avoid side effects a CB1-selective compound is desirable.

$\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *canabis sativa* (marijuanan), which is used in medicine since ages (R. Mechoulam (Ed.) in "*Cannabinoids as therapeutic Agents*", 1986, pp. 1–20, CRC Press). $\Delta^9$-THC is a non-selective CB1/2 receptor agonist and is available in the USA as dronabinol (marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539–545, E. M. Williamson, F. J. Evans, Drugs 60 (6) (2000) 1303–1314).

Anandamide (arachidonylethanolamide) was identified as the endogenous ligand (agonist) for the CB1 receptor (R. G. Pertwee, Curr. Med. Chem., 6 (8) (1999) 635–664; W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946–9). Anandamide and 2-arachidonoylglycerol (2-AG) modulate at the presynaptic nerve terminal negatively adenylate cyclase and voltage-sensitive $Ca^{2+}$ channels and activates the inwardly rectifying $K^+$ channel (V. Di Marzo, D. Melck, T. Bisogno, L. De Petrocellis, Trends in Neuroscience 21 (12) (1998) 521–8), thereby affecting neurotransmitter release and/or action, which decreases the release of neurotransmitter (A. C. Porter, C. C. Felder, Pharmacol. Ther., 90 (1) (2001) 45–60).

Anandamide as $\Delta^9$-THC also increases feeding through CB1 receptor-mediated mechanism. CB1 receptor selective antagonists block the increase in feeding associated with administration of anandamide (C. M. Williams, T. C. Kirkham, Psychopharmacology 143 (3) (1999) 315–317; C. C. Felder, E. M. Briley, J. Axelrod, J. T. Simpson, K. Mackie, W. A. Devane, Proc. Natl. Acad. Sci. U.S.A. 90 (16) (1993) 7656–60) and caused appetite suppression and weight loss (G. Colombo, R. Agabio, G. Diaz, C. Lobina, R. Reali, G. L. Gessa, Life Sci. 63 (8) (1998) L113-PL117).

Leptin is the primary signal through which the hypothalamus senses nutritional state and modulates food intake and energy balance. Following temporary food restriction, CB1 receptor knockout mice eat less than their wild-type littermates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822–825).

SR-141716A, a CB1 selective antagonist/inverse agonist is undergoing currently phase III clinical trials for the treatment of obesity. In a double blind placebo-controlled study, at the doses of 5, 10 and 20 mg daily, SR 141716 significantly reduced body weight when compared to placebo (F. Barth, M. Rinaldi-Carmona, M. Arnone, H. Heshmati, G. Le Fur, "*Cannabinoid antagonists: From research tools to potential new drugs.*" Abstracts of Papers, 222nd ACS National Meeting, Chicago, Ill., United States, Aug. 26–30, 2001).

Other compounds which have been proposed as CB1 receptor antagonists respectively inverse agonists are aminoalkylindoles (AAI; M. Pacheco, S. R. Childers, R. Arnold, F. Casiano, S. J. Ward, J. Pharmacol. Exp. Ther. 257 (1) (1991) 170–183), like 6-bromo- (WIN54661; F. M. Casiano, R. Arnold, D. Haycock, J. Kuster, S. J. Ward, NIDA Res. Monogr. 105 (1991) 295–6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115–118; R. Pertwee, G. Griffin, S. Fernando, X. Li, A. Hill, A. Makriyannis, Life Sci. 56 (23–24) (1995) 1949–55). Arylbenzo[b]thiophene and benzo[b]furan (LY320135, C. C. Felder, K. E. Joyce, E. M. Briley, M. Glass, K. P. Mackie, K. J. Fahey, G. J. Cullinan, D. C. Hunden, D. W. Johnson, M. O. Chaney, G. A. Koppel, M. Brownstein, J. Pharmacol. Exp. Ther. 284 (1) (1998) 291–7) disclosed in WO9602248, U.S. Pat. No. 5,596,106, 3-alkyl-(5,5-diphenyl)imidazolidinediones (M. Kanyonyo, S. J. Govaerts, E. Hermans, J. H. Poupaert, D. M. Lambert, Bioorg. Med. Chem. Lett. 9 (15) (1999) 2233–2236.) as well as 3-alkyl-5-arylimidazolidinediones (F. Ooms, J. Wouters, O. Oscaro. T. Happaerts, G. Bouchard, P.-A. Carrupt, B. Testa, D. M. Lambert, J. Med. Chem. 45 (9) (2002) 1748–1756) are known to antagonize the CB1 receptor respectively act as an inverse agonist on the hCB1 receptor. WO0015609 (FR2783246-A1), WO0164634 (FR2805817-A1), WO0228346, WO0164632 (FR2805818-A1), WO0164633 (FR2805810-A1) disclosed substituted 1-bis (aryl)methyl-azetidines derivatives as antagonists of CB1. In WO0170700, WO02076949, and WO0276949A1 4,5-dihydro-1H-pyrazole derivatives are described as CB1 antagonists. In several patents and publications bridged and non-bridged 3-pyrazolecarboxamide derivatives are disclosed as CB1 antagonists/inverse agonists (WO0132663, WO0046209, WO9719063, EP658546, EP656354, U.S. Pat. No. 5,624,941, EP576357, U.S. Pat. No. 3,940,418, WO03020217, WO0335005, J. M. Mussinu et al., Bioorg. Med. Chem. 2003, 11, 251; S. Ruiu et al., J. Pharm. Expt. Ther., 2003, 306, 363). Pyrrole CB1 cannabinoid receptor agonists have been described in G. Tarzia et al., Bioorg. Med. Chem. 2003, 11, 3965. Phenethyl amides have been claimed as CB1 cannabinoid receptor antagonists/inverse agonists in WO03077847, WO03082190, WO03086288 and WO03087037. Various aza heterocycles (imidazoles, triazoles and thiazoles) are described in WO0337332, WO03040107, WO03063781, WO03082833 and WO03078413. Diphenylpyrazine carboxamides are described in WO03051850, diphenylpyridine carboxamides in WO03084930 and diphenylbenzene carboxamides in WO03084943.

3

It is an object of this invention to provide selective, directly acting CB1 receptor antagonists respectively inverse agonists. Such antagonists/inverse antagonists are useful in medical therapy, particularly in the treatment and/or prevention of diseases which are associated with the modulation of CB1 receptors.

SUMMARY OF THE INVENTION

The present invention is concerned with novel spiro-pentacyclic compounds of the general formula (I):

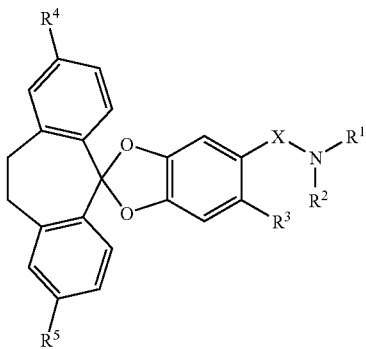

(I)

their manufacture, pharmaceutical compositions containing them and their use as medicaments. The compounds of the present invention are useful in treating obesity and other disorders.

DETAILED DESCRIPTION OF THE INVENTION

The present invention comprises compounds of formula (I):

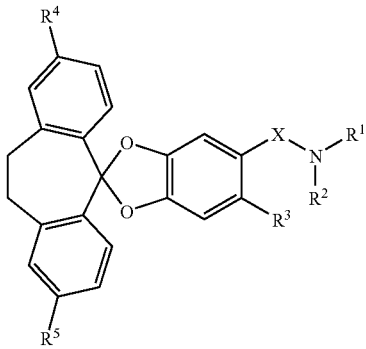

(I)

wherein
$R^1$ and $R^2$ together with the nitrogen atom to which they are attached form a 4-, 5-, 6- or 7-membered monocyclic, saturated heterocyclic ring which may optionally contain one or two further heteroatoms independently selected from O, N and S;
$R^3$ is hydrogen, halogen, lower alkyl or cyano;
$R^4$ and $R^5$ are each independently halogen; and
X is —C(O)— or —SO$_2$—;
or a pharmaceutically acceptable salt thereof.

4

Unless otherwise indicated, the following definitions are set forth to illustrate and define the meaning and scope of the various terms used to describe the invention herein.

In this specification the term "lower" is used to mean a group consisting of one to eight, preferably of one to four carbon atom(s).

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to eight carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "halogen" refers to fluorine, chlorine, bromine and iodine, preferably to chlorine and fluorine.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms.

Preferred salts with acids are formates, maleates, citrates, hydrochlorides, hydrobromides and methanesulfonic acid salts, with hydrochlorides being especially preferred.

In one embodiment, the present invention relates to a compound of formula (I) as defined above, wherein $R^1$ and $R^2$ together with the nitrogen atom to which they are attached form a 4-, 5-, 6- or 7-membered monocyclic, saturated heterocyclic ring which may optionally contain one or two further heteroatoms independently selected from O, N and S. In a preferable embodiment, $R^1$ and $R^2$ together with the nitrogen atom to which they are attached form a 6-membered monocyclic, saturated heterocyclic ring which may optionally contain one further oxygen atom in the ring. Most preferable heterocyclic rings formed by $R^1$ and $R^2$ together with the nitrogen atom to which they are attached are piperidinyl and morpholino.

In another embodiment, the present invention relates to a compound of formula (I) as defined above, wherein $R^3$ is hydrogen, halogen, lower alkyl or cyano. Preferable lower alkyl residue $R^3$ is methyl. Preferable halogen residues $R^3$ are fluoro and chloro, with fluoro being especially preferred. Preferably $R^3$ is hydrogen or halogen such as fluoro.

In another embodiment, the present invention relates to a compound of formula (I) as defined above, wherein $R^4$ and $R^5$ are each independently halogen. Preferably, $R^4$ and $R^5$ are both fluoro, or $R^4$ and $R^5$ are both chloro. Most preferably, $R^4$ and $R^5$ are fluoro.

In another embodiment, the present invention relates to a compound of formula (I) as defined above, wherein X is —C(O)— or —SO$_2$—. Preferably, X is —C(O)—.

Preferred compounds of general formula (I) are the compounds selected from the group consisting of:
4-[(2',8'-dichloro-6-fluoro-10',11'-dihydrospiro[1,3-benzo-dioxole-2,5'-[5H]dibenzo[a,d]cyclohepten]-5-yl)carbonyl]-morpholine,
4-[(2',8'-dichloro-10',11'-dihydrospiro[1,3-benzodioxole-2, 5'-[5H]dibenzo[a,d]cyclohepten]-5-yl)carbonyl]-piperidine, 4-[(2',8'-dichloro-6-fluoro-10',11'-dihydrospiro[1,3-benzo-dioxole-2,5'-[5H]dibenzo[a,d]cyclohepten]-5-yl)carbo-nyl]-piperidine, 4-[(2',8'-dichloro-6-fluoro-10',11'-dihydrospiro[1,3-benzo-dioxole-2,5'-[5H]dibenzo[a,d]cyclohepten]-5-yl)sulfo-nyl]-morpholine, 4-[(2',6,8'-trifluoro-10',11'-dihydrospiro[1,3-benzodioxole-2,5'-[5H]dibenzo[a,d]cyclohepten]-5-yl)carbonyl]-mor-pholine, 4-[(2',6,8'-trifluoro-10',11'-dihydrospiro[1,3-benzodioxole-2,5'-[5H]dibenzo[a,d]cyclohepten]-5-yl)carbonyl]-piperi-dine, and pharmaceutically acceptable salts thereof.

Processes for the manufacture of compounds of formula I are also an object of the invention. Thus, the invention further relates to a process for the manufacture of com-pounds of formula (I), which process comprises:

(a) ketalizing a compound of formula (A)

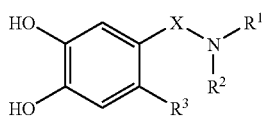

wherein $R^1$, $R^2$, $R^3$ and X are as defined hereinbefore;

with a compound of formula (B)

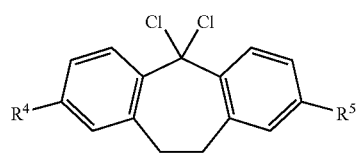

wherein $R^4$ and $R^5$ are as defined herein before; or (b) reacting a compound of formula (A)

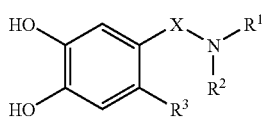

wherein $R^1$, $R^2$, $R^3$ and X are as defined in claim 1;

with a compound of formula (C)

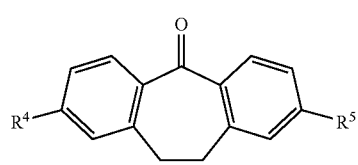

wherein $R^4$ and $R^5$ are as defined herein before; or (c) reacting a compound of formula (A)

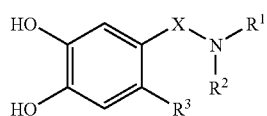

wherein $R^1$, $R^2$, $R^3$ and X are as defined herein before;

with a compound of formula (D)

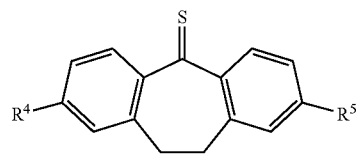

wherein $R^4$ and $R^5$ are as defined herein before.

In detail, the compounds of formula (I) wherein $R^1$ to $R^5$ and X are as previously defined may be prepared using the general methods depicted in Scheme 1 as further described below.

According to Scheme 1, a catechol intermediate of for-mula (A) can be ketalized with a bis-substituted dichlo-romethane derivative of formula (B) in an inert solvent (e.g. toluene or pyridine) or neat, with or without the presence of a base (e.g. pyridine) at elevated temperature (e.g. >100° C.) to yield product I. Alternatively, a compound of formula (I) may be prepared by reacting the catechol intermediate of formula (A) with a ketone of formula (C) at elevated temperature (e.g. >150° C.) neat or in an inert solvent (e.g. toluene) with or without the removal of water by distillation, azeotropic distillation or addition of drying agents (e.g. molecular sieves or 2,2-dimethoxypropane) by methods known in the art (see e.g. T. R. Kelly, A. Szabados, Y.-J. Lee, J. Org. Chem. 62 (2) (1997) 428). Alternatively, a compound of formula (I) may be prepared by reacting the catechol intermediate of formula (A) with a thioketone of formula (D) neat or in an inert solvent (e.g. acetonitrile) with or without the presence of a base (e.g. triethylamine) with a metal salt (e.g. $Ag^I$) by methods known in the art (see e.g. I. Shibuya, E. Katoh, Y. Gama, A. Oishi, Y. Taguchi and T. Tsuchiya, Heterocycles, 43 (1996) 851).

Scheme 1:

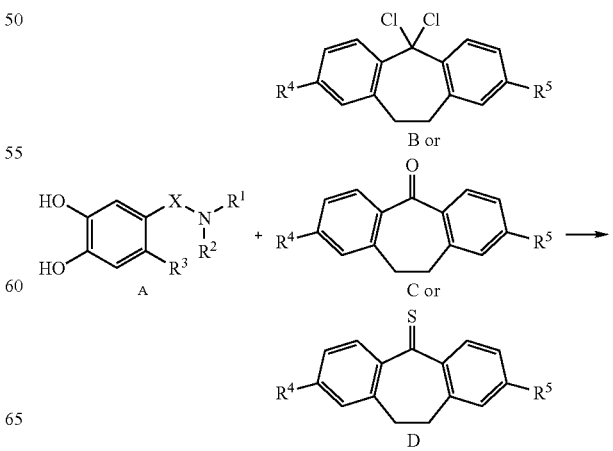

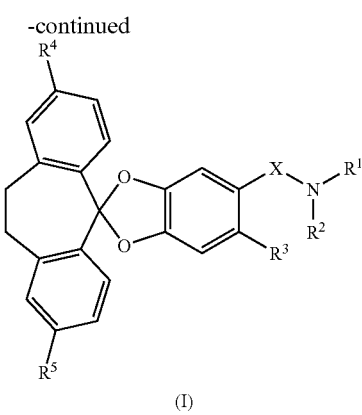

Alternatively, a compound of formula (I) may be prepared by reacting a diazo-compound of formula (E) with a 1,2-diketone of formula (F) (Scheme 2) by methods known in the art (see e.g. J. M. Fox, N. R. Goldberg and T. J. Katz, J. Org. Chem., 1998, 63, 7456). Diazo-compounds of formula (E) are available from the corresponding hydrazone by methods known in the art; 1,2-diketones of formula (F) are available from catechols of formula (A) by methods known in the art.

Scheme 2:

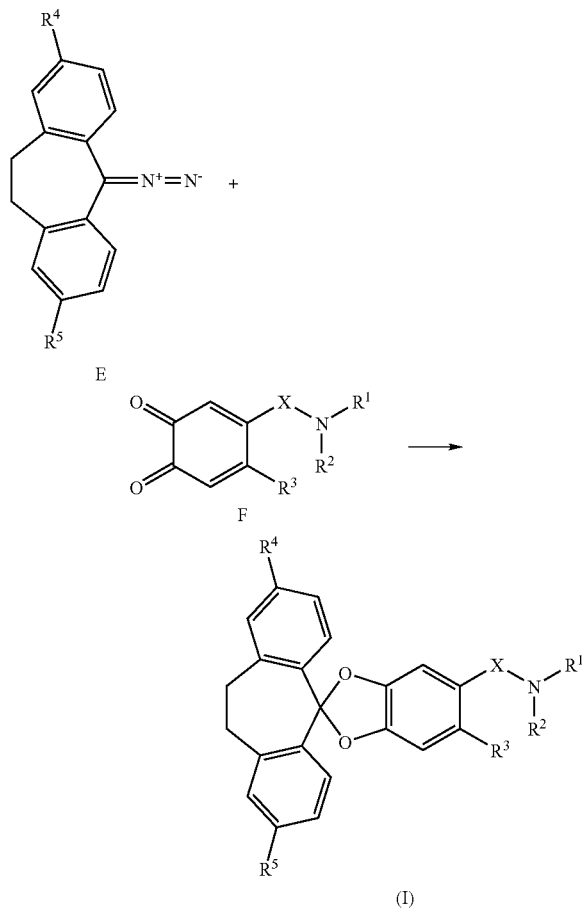

The bis-substituted dichloromethane derivatives of formula (B) may be prepared by methods known in the art from the corresponding ketone by reaction with thionyl chloride in the presence of DMF or another N-formylated agent, by reaction with phosphorus pentachloride with or without the presence of a suitable solvent, e.g. phosphorus oxide chloride (Scheme 3).

The ketones of formula (C) may be prepared by electrophilic aromatic substitution of the derivative (G) with oxalyl chloride in the presence of a Lewis acid (e.g. aluminium trichloride) in an inert solvent (e.g. carbon disulfide) (e.g. M. R. Pavia et al., Journal of Medicinal Chemistry 1992, 35, 4238–48), by intramolecular cyclisation of a carboxylic acid derivative of formula (H) in the presence of a Lewis acid (e.g. polyphosphoric acid) with or without an inert solvent (e.g. 1,2-dichloroethane) (e.g. WO9854180).

The thioketones of formula (D) may be easily prepared from the corresponding ketones (C) by reaction with a suitable thionation reagent (e.g. phosphorus pentasulfide), according to methods known in the art, in the presence of a suitable solvent (e.g. toluene) with or without the presence of a silane (e.g. hexamethyldisiloxane) (e.g. T. J. Curphey, J. Org. Chem., 2002, 67, 6461).

Scheme 3:

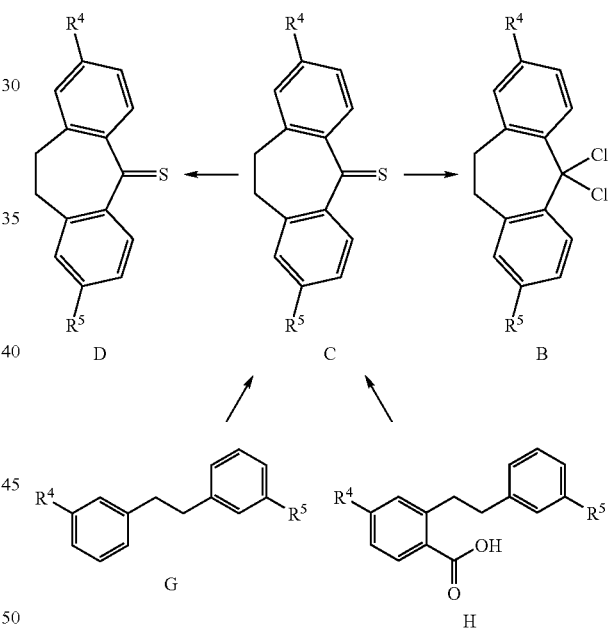

Catechols of formula A can be easily prepared from the corresponding diphenylmethylene protected ketals of formula (Ia) by treatment with an acid (e.g. trifluoroacetic acid) in a suitable inert solvent (e.g. methylene chloride) or by treatment with an acid (e.g. trifluoroacetic acid) in the presence of a suitable reducing agent (e.g. triethylsilane), neat or with a suitable inert solvent (e.g. methylene chloride).

Alternatively, a catechol of formula A can be easily prepared from a corresponding bis-benzyl protected catechol of formula (J) by reduction (e.g hydrogenation in the presence of a suitable catalyst, e.g. palladium on carbon, by means known in the art). Alternatively, a catechol derivative of formula (K) can be coupled with an appropriate amine in a suitable inert solvent (e.g. DMF, methylene chloride, pyridine or THF) in the presence of a base (e.g. triethyl amine). Either the corresponding acid chlorides (X=CO, Z=Cl) respectively the corresponding sulfonyl chlorides (X=SO$_2$, Z=Cl) or the corresponding carboxylic acids (X=CO, Z=OH) after activation with an appropriate coupling agent (e.g. carbonyldiimidazole) are used for the preparation of catechols of formula (A) by methods known in the art (Scheme 4). Diphenylmethylene protected ketals of formula (Ia), bis-benzyl protected catechol of formula (J) and catechol derivative of formula (K) may be prepared by methods analogous to those described in the literature.

In another embodiment, the invention relates to a method for the treatment and/or prophylaxis of diseases which are associated with the modulation of CB1 receptors, which method comprises administering a compound as defined above to a human being or animal.

The invention further relates to the use of compounds as defined above for the treatment and/or prophylaxis of diseases which are associated with the modulation of CB1 receptors.

In addition, the invention relates to the use of compounds as defined above for the preparation of medicaments for the Scheme 4:

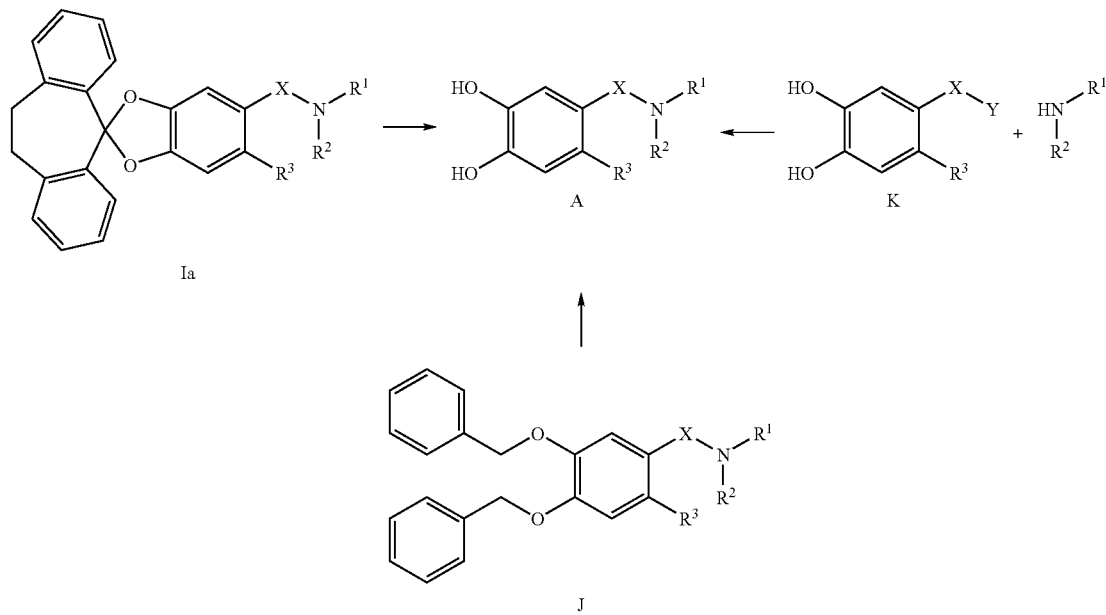

Some compounds of formula (I) may possess asymmetric centres and are therefore capable of existing in more than one stereoisomeric form. The invention thus also relates to compounds in substantially pure isomeric form at one or more asymmetric centres as well as mixtures, including racemic mixtures, thereof. Such isomers may be prepared by asymmetric synthesis, for example using chiral intermediate, or mixtures may be resolved by conventional methods, eg., chromatography (chromatography with a chiral adsorbent or eluant), or use of a resolving agent.

It will be appreciated, that the compounds of general formula (I) in this invention may be derivatised at functional groups to provide derivatives which are capable of conversion back to the parent compound in vivo.

As described above, the compounds of formula (I) or pharmaceutically acceptable salts thereof can be used as therapeutically active substances, especially as therapeutically active substances for the treatment and/or prophylaxis of diseases which are associated with the modulation of the CB1 receptors. In one embodiment, the invention therefore relates to compounds as defined above for use as therapeutic active substances, particularly as therapeutic active substances for the treatment and/or prophylaxis of diseases which are associated with the modulation of CB1 receptors.

The invention also relates to pharmaceutical compositions comprising a compound as defined above and a pharmaceutically acceptable carrier and/or adjuvant.

treatment and/or prophylaxis of diseases which are associated with the modulation of CB1 receptors. Such medicaments comprise a compound as defined above.

In this context, the expression 'diseases associated with modulation of CB1 receptors' means diseases which can be treated and/or prevented by modulation of CB1 receptors. Such diseases encompass, but are not limited to, psychic disorders, especially anxiety and anxiety disorders, psychosis, schizophrenia, depression, substance abuse disorders including abuse of psychotropes, for example for the abuse and/or dependence of substances, including alcohol dependency and nicotine dependency, neuropathies, migraine, stress, epilepsy, dyskinesias, Parkinson's disease, amnesia, memory and cognitive disorders, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, infections, cancer, demyelinisation related disorders, neuroinflammation, in particular in atherosclerosis, or the Guillain-Barré syndrome, viral encephalitis, cerebral vascular incidents and cranial trauma.

In a preferable aspect, the expression 'diseases associated with modulation of CB1 receptors' relates to eating disorders, obesity, diabetes type II or non insulin dependent diabetes (NIDD), neuroinflammation, diarrhea, abuse and/or dependence of a substances, including alcohol dependency and nicotine dependency. In a more preferable aspect, the said term related to eating disorders, obesity, diabetes type II or non insulin dependent diabetes (NIDD), abuse and/or dependence of a substances, including alcohol dependency and nicotine dependency, with obesity being especially preferred.

It is a further preferred object to provide a method of treatment or prevention of Type II diabetes (non-insulin dependent diabetes mellitus (NIDDM) in a human which comprises administration of a therapeutically effective amount of a compound according to formula (I) in combination or association with a therapeutically effective amount of a lipase inhibitor, particularly, wherein the lipase inhibitor is orlistat. Also an object of the invention is the method as described above for the simultaneous, separate or sequential administration of a compound according to formula (I) and a lipase inhibitor, particularly tetrahydrolipstatin.

It is a further preferred object to provide a method for the treatment or prevention of obesity and obesity related disorders which comprises administration of a therapeutically effective amount of a compound according to formula (I) in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Most preferable anorectic agents are sibutramine and phentermine.

Suitable selective serotonin reuptake inhibitors of use in combination with a compound of the present invention include fluoxetine, fluvoxamine, paroxetine and sertraline, and pharmaceutically acceptable salts thereof.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117: 149–153, 1990; Morris, J. Neurosci. Methods 11: 47–60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escapes from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161: 442–448, 2002; Campbell et al., Exp. Clin. Psychopharmacol. 8: 312–25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated.

Administration of this second compound prior to the session can either potentiate, extinguish, or produce no change to the self-administrating behavior.

The following tests were carried out in order to determine the activity of the compounds of formula (I).

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glassfiber filters. Radioactivity on the filter was measured by liquid scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound of bound and free ligand was performed by filtration over glassfiber filters. Radioactivity on the filter was measured by liquid scintillation counting.

The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871). The stable expression of the human cannabinoid receptor in cell systems was first described in Nature 1990, 346, 561–564 (CB1) and Nature 1993, 365, 61–65 (CB2) respectively. Adenylyl cyclase was stimulated using forskolin and measured by quantifying the amount of accumulated cyclic AMP. Concomitant activation of CB1 receptors by CB1 receptor agonists (e.g. CP-55,940 or (R)-WIN-55212–2) can attenuate the forskolin-induced accumulation of cAMP in a concentration dependent manner.

This CB1 receptor mediated response can be antagonised by CB1 receptor antagonists such as the compounds of the invention.

The compounds of formula (I) show an excellent affinity for the CB1 receptor, determined with the experimental conditions described in Devane et. al. Mol. Pharmacol. 34 (1988) 605–613. The compounds of the present invention or the pharmaceutically acceptable salts or solvates are antagonists and selective for the CB1 receptor with affinities below $IC_{50}=5$ µM, preferably below $IC_{50}=2$ µM. They exhibit at least a 10 fold selectivity against the CB2 receptor.

| Compound of Example | $IC_{50}$ [µM] |
|---|---|
| 1 | 0.013 |
| 2 | 0.018 |

Effect of CB1 Receptor Antagonist/Inverse Agonist on CP 55,940-induced Hypothermia in NMRI Mice Animals Male NMRI mice were used in this study and were obtained from Research Consulting Company Ltd (RCC) of Füllinsdorf (Switzerland). Mice, weighing 30–31 g were used in this study. Ambient temperature is approximately 20–21° C. and relative humidity 55–65%. A 12 hours light-dark cycle is maintained in the rooms with all tests being performed during the light phase. Access to tap water and food are ad libitum.

Method

All measurements were made between 12:00 am and 5:00 pm. Mice were brought in this environment and habituated for at least two hours before the start of the experiment. They had always free access to food and water. For each dose, 8 mice were used. Rectal body temperature measurements were recorded by mean of a rectal probe (RET2 of Physitemp) and digital thermometer (Digi-sense n°8528–20 of Cole Parmer, Chicago USA). The probe was inserted about 3.5 cm in each mouse.

The body temperature was taken 15 min before administration of either Vehicle or CB1 receptor antagonist/inverse agonist. 30 or 90 min after i.p. or p.o. administration of this compound, respectively, rectal body temperature was recorded in order to evaluate any influence of the compound itself. The CB receptor agonist CP 55,940 (0.3 mg/kg) was immediately administered intravenously, then 20 min after i.v. administration of CP 55940, body temperature was again measured.

The in vivo Activity of Compounds of Formula (I) was Assessed for Their Ability to Regulate Feeding Behaviour by Recording Food Consumption in Food Deprived Animals.

Rats were trained to have access to food for 2 h per day and were food deprived for 22 h. When they were trained under this schedule, the amount of food taken every day during these 2 h food intake session was consistent day after day.

To test the ability of compounds of formula (I) to decrease food intake, 8 animals were used in a cross-over study. Rats were individually housed in Plexiglas boxes with a grid on the floor and a paper was placed below the cage floor to collect any spillage. A food dispenser (beaker) filled with a pre-weighed amount of food was presented to them for 2 h. At the end of the food intake session, rats returned to their home cage. Each rat was weighed before the start of the experiment and the amount of food consumed during this 2 h food intake session was recorded. Either various doses of test compound or vehicle was administered orally 60 min before the 2 h food intake session. A positive control Rimonabant (SR141716) was included in the experiment. An Anova analysis with repeated measures was used followed by a posthoc test Student Neumann-Keuls. *$P<0.05$ compared to Saline-treated rats.

Furthermore the utility of compounds of formula (I) in diseases or disorders may be demonstrated in animal disease models that have been reported in the literature. The following are examples of such animal disease models: a) reduction of sweet food intake in marmosets (Behavioural Pharm, 1998, 9,179–181); b) reduction of sucrose and ethanol intake in mice (Psychopharm. 1997, 132, 104–106); c) increased motor activity and place conditioning in rats (Psychopharm. 1998, 135, 324–332; Psychopharmacol 2000, 151: 25–30); d) spontaneous locomotor activity in mice (J. Pharm. Exp. Ther. 1996, 277, 586–594); e) reduction in opiate self-administration in mice (Sci. 1999, 283, 401–404);

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1–500 mg, preferably 1–100 mg, of a compound of formula (I).

The following Examples serve to illustrate the present invention in more detail. They are, however, not intended to limit its scope in any manner.

EXAMPLES

MS=mass spectrometry, EI=electron impact, ISP=ion spray (positive ion). All experiments were conducted under an inert atmosphere (nitrogen or argon).

Example 1

Preparation of 4-[(2',8'-dichloro-6-fluoro-10',11'-dihydrospiro[1,3-benzodioxole-2,5'-[5H]dibenzo[a,d]cyclohepten]-5-yl)carbonyl]-morpholine Preparation of 4-bromo-5-fluoro-benzene-1,2-diol To a cooled (−78° C.) solution of 4-fluoroveratrole (5.0 g, 32 mmol) in dichloromethane (106 ml) was slowly added a solution of boron trichloride in dichloromethane (1M, 96 ml, 96 mmol, 3.0 eq.). The reaction mixture was warmed to 20° C. and stirred overnight. The reaction mixture was poured into ice water, extracted with ethyl acetate (3 times). The combined organic layer was washed with an aqueous solution of sodium bicarbonate, dried over sodium sulfate and filtered. The volatiles were removed in vacuo. The brown solid was diluted with chloroform (50 ml) and dichloromethane (10 ml). A solution of bromine in carbon tetrachloride (5 ml) was slowly added. After stirring 3 h at room temperature, the volatiles were removed in vacuo. Purification by flash chromatography afforded the title compound (6.51 g, 98%) as a brown solid.

ISP MS: m/e=207.9 ([M+H]$^+$).

Preparation of 5-bromo-6-fluoro-2,2-diphenyl-benzo[1,3]dioxole

A mixture of 4-bromo-5-fluoro-benzene-1,2-diol (12 g, 58.0 mmol) and diphenyldichloromethane (1.2 eq., 16.50 g) was stirred at room temperature until gaseous evolution ceased. The mixture was heated with stirring at 180° C. for 20 min. The reaction mixture was allowed to cool to room temperature, diluted with methanol (50 ml) and vigorously stirred. The precipitated product was collected by filtration and dissolved in toluene (50 ml). Methanol (100 ml) was added and the mixture stirred 30 min at room temperature. The precipitated product was collected by filtration (yield 10.3 g, 48%), a further batch (6.4 g, 30%) was recovered from the mother liquors.

ISP MS: m/e=370.0 ([M+H$^+$]).

Preparation of (6-fluoro-2,2-diphenyl-benzo[1,3] dioxol-5-yl)-morpholin-4-yl-methanone To a cooled (−78° C.) solution of 5-bromo-6-fluoro-2,2-diphenyl-benzo[1,3]dioxole (17.59 g, 47.4 mmol) in diethyl ether (300 ml) was slowly added a solution of n-butyl lithium in hexanes (1.6M, 30 ml, 48 mmol, 1.0 eq.). The reaction mixture was stirred 1 h at −78° C. before the addition of 4-morpholinecarbonylchloride (8.5 g, 56.9 mmol, 1.2 eq.). The reaction mixture was allowed to warm to 20° C. and poured into an aqueous solution of sodium bicarbonate. The aqueous layer was extracted with ethyl acetate. The combined organic layers were washed with brine. Volatiles were removed in vacuo. Purification by flash chromatography afforded (6-fluoro-2,2-diphenyl-benzo[1,3]dioxol-5-yl)-morpholin-4-yl-methanone compound (13.0 g, 68%) as a light yellow solid.

ISP MS: m/e=406.2 ([M+H]$^+$).

Preparation of (2-fluoro-4,5-dihydroxy-phenyl)-morpholin-4-yl-methanone

To a cooled (ice-bath) solution of (6-fluoro-2,2-diphenyl-benzo[1,3]dioxol-5-yl)-morpholin-4-yl-methanone (5.70 g, 14.06 mMol) in trifluoroacetic acid (60 ml) was added triethylsilane (2.1 eq, 4.7 ml) over 10 min. The mixture was stirred 20 min at 0° C. and 4 h at room temperature. The volatiles were removed under reduced pressure and the residue purified by column chromatography on silica gel (2:1 ethyl acetate/heptane-ethyl acetate-10:1 ethyl acetate/ methanol) to afford (2-fluoro-4,5-dihydroxy-phenyl)-morpholin-4-yl-methanone as liht brown solid (3.19 g, 94%).
ISP MS: m/e=242.2 ([M+H]+).

Preparation of 2,8-dichloro-10,11-dihydro-dibenzo [a,d]cycloheptene-5-thione

To a stirred solution of 2,8-dichloro-10,11-dihydro-dibenzo[a,d]cycloheptene-5-one (0.70 g, 2.53 mMol) in toluene (20 ml) were added phosphorus pentasulfide (1 eq, 561 mg) and hexamethyldisiloxane (1 eq, 0.54 ml). The mixture was heated 3 h at reflux and allowed to cool to room temperature. The mixture was filtered through a pad of silica gel (70 g) and washed through with 8:1 heptane/ethyl acetate. Evaporation of the solvent under reduced pressure afforded 2,8-dichloro-10,11-dihydro-dibenzo[a,d]cycloheptene-5-thione as a blue solid (710 mg, 95%) that was used without further purification.
EI MS: m/e=292.0 ([M]+).

Preparation of 4-[(2',8'-dichloro-6-fluoro-10',11'-dihydrospiro[1,3-benzodioxole-2,5'-[5H]dibenzo[a, d]cyclohepten]-5-yl)carbonyl]-morpholine To a solution of (3,4-dihydroxy-phenyl)-morpholin-4-yl-methanone (360 mg, 1.49 mMol) in acetonitrile (14 ml) were added 2,8-dichloro-10,11-dihydro-dibenzo[a,d]cycloheptene-5-thione (1.5 eq, 657 mg), silver trifluoroacetate (2.5 eq, 824 mg) and quinuclidine (4 eq, 667 mg). The mixture was heated 4 h at reflux, cooled to room temperature, filtered over diatomaceous earth (Dicalite), washed through with ethyl acetate and evaporated under reduced pressure. The residue was purified by column chromatography on silica gel (1:0 to 10:1 dichloromethane/ethyl acetate) to afford the product as an off-white foam (396 mg, 53%).
EI MS: m/e=499.1 ([M]+).

Example 2

Preparation of 4-[(2',8'-dichloro-10',11'-dihydrospiro [1,3-benzodioxole-2,5'-[5H]dibenzo[a,d]cyclohepten]-5-yl)carbonyl]-piperidine The title compound was prepared in accordance with the general method of Example 1f from (3,4-dihydroxy-phenyl)-piperidin-4-yl-methanone and 2,8-dichloro-10,11-dihydro-dibenzo[a,d]cycloheptene-5-thione (Example 1e). Yellow solid.
EI MS: m/e=478.2 ([M]+).

Example 3

Preparation of 4-[(2',8'-dichloro-6-fluoro-10',11'-dihydrospiro[1,3-benzodioxole-2,5'-[5H]dibenzo[a, d]cyclohepten]-5-yl)carbonyl]-piperidine Preparation of (6-fluoro-2,2-diphenyl-benzo[1,3] dioxol-5-yl)-piperidin-1-yl-methanone The title compound was produced in accordance with the general method of Example 1c from 5-bromo-6-fluoro-2,2-diphenyl-benzo[1,3]dioxole (Example 1b) and 1-piperidinecarbonyl chloride. Colorless semisolid.
MS: m/e=404.3 ([M+H]+).

Preparation of (2-fluoro-4,5-dihydroxy-phenyl)-piperidin-1-yl-methanone

The title compound was produced in accordance with the general method of Example 1d from (6-fluoro-2,2-diphenyl-benzo[1,3]dioxol-5-yl)-piperidin-1-yl-methanone. Colorless semisolid.
MS: m/e=240.2 ([M+H]+).

Preparation of 4-[(2',8'-dichloro-6-fluoro-10',11'-dihydrospiro[1,3-benzodioxole-2,5'-[5H]dibenzo[a, d]cyclohepten]-5-yl)carbonyl]-piperidine The title compound was prepared in accordance with the general method of Example 1f from (2-fluoro-4,5-dihydroxy-phenyl)-piperidin-1-yl-methanone and 2,8-dichloro-10,11-dihydro-dibenzo[a,d]cycloheptene-5-thione (Example 1e). Light yellow gum.
ISP MS: m/e=498.2 ([M+H]+).

Example 4

Preparation of 4-[(2',8'-dichloro-6-fluoro-10',11'-dihydrospiro[1,3-benzodioxole-2,5'-[5H]dibenzo[a, d]cyclohepten]-5-yl)sulfonyl]-morpholine Preparation of 2-fluoro-4,5-dimethoxy-benzenesulfonyl chloride To a suspension of sulfur trioxide N,N-dimethylformamide complex (4.108 g, 27 mmol) in 1,2-dichloroethane was added 4-fluoroveratrole (3.49 g, 22 mmol) dropwise. The mixture was slowly heated to 85° C. in an oil bath. After 2.5 h, the solids had dissolved to afford a golden yellow solution. A trace of starting material was still present and heating was continued for a further 4.5 h. The oil bath was removed and thionyl chloride (1.95 ml, 27 mmol) added dropwise. The mixture was heated 4 h at 85° C. and allowed to cool to room temperature. The solution was poured into water and extracted with dichloromethane (3×50 ml), the combined organics washed with water, dried over magnesium sulfate and evaporated. Remaining traces of N,N-dimethylformamide were removed azeotropically with toluene to afford the product as an off-white solid that was used without further purification.
EI MS: m/e=254.0 ([M]+).

Preparation of 1-(2-fluoro-4,5-dimethoxy-benzenesulfonyl)-morpholine

To a solution of 2-fluoro-4,5-dimethoxy-benzenesulfonyl chloride (5.30 g, 20.81 mMol) in dichloromethane (30 ml) was added morpholine (2.1 eq, 3.81 ml) dropwise (Exothermic reaction). The mixture was stirred overnight at room temperature and filtered through a pad of silica gel and eluted with ethyl acetate. The solvent was evaporated under reduced pressure to afford 1-(2-fluoro-4,5-dimethoxy-benzenesulfonyl)-morpholine as a pale yellow solid that was used without further purification.
EI MS: m/e=305.1 ([M]+).

Preparation of 4-fluoro-5-(morpholine-1-sulfonyl)-benzene-1,2-diol

To a cooled (ice-bath) solution of 1-(2-fluoro-4,5-dimethoxy-benzenesulfonyl)-morpholine (837 mg, 2.74 mMol) in dichloromethane (25 ml) was added a 1M solution of boron tribromide in dichloromethane (2 eq, 5.48 ml). The mixture was stirred overnight at room temperature and poured into 1M aqueous potassium dihydrogenphosphate and ice. After stirring 1 h, the phases were separated and the aqueous phase extracted with ethyl acetate. The combined organic phases were washed with brine, dried over magnesium sulfate and evaporated. The residue was purified by column chromatography on silica gel (19:1 chloroform/ethanol eluant) to afford 4-fluoro-5-(morpholine-1-sulfonyl)-benzene-1,2-diol as a brown oil (564 mg, 74%) which solidified upon standing in the refrigerator.

MS: m/e=276.0 ([M–H]$^+$).

Preparation of 4-[(2',8'-dichloro-6-fluoro-10',11'-dihydrospiro[1,3-benzodioxole-2,5'-[5H]dibenzo[a,d]cyclohepten]-5-yl)sulfonyl]-morpholine The title compound was prepared in accordance with the general method of Example 1f from 4-fluoro-5-(morpholine-1-sulfonyl)-benzene-1,2-diol and 2,8-dichloro-10,11-dihydro-dibenzo [a,d]cycloheptene-5-thione (Example 1e).

EI MS: m/e=535.1 ([M]$^+$).

Example 5

Preparation of 4-[(2',6,8'-trifluoro-10',11'-dihydrospiro[1,3-benzodioxole-2,5'-[-5H]dibenzo[a,d]cyclohepten]-5-yl)carbonyl]-morpholine Preparation of 2,8-difluoro-10,11-dihydro-dibenzo[a,d]cycloheptene-5-one To a cooled (dry-ice/acetone bath) suspension of anhydrous aluminium trichloride (5 eq, 45.82 g, 0.34 Mol) in carbon disulfide (450 ml) was added oxalyl chloride (4 eq, 23.58 ml) dropwise. The mixture was allowed to reach room temperature before the slow addition of 1,1'-(1,2-ethanediyl)bis[3-fluorobenzene](1 eq, 15.00 g) as a solution in carbon disulfide (20 ml). The mixture was heated overnight at 35° C. and diluted with chloroform (400 ml). The mixture was cooled (ice-bath) and water (400 ml) slowly added. The phases were separated, the aqueous phase extracted with chloroform and the combined organic phases dried over magnesium sulfate and evaporated under reduced pressure. The residue was purified by column chromatography on silica gel (15:1 heptane/ethyl acetate) to afford 2,8-difluoro-10,11-dihydro-dibenzo[a,d]cycloheptene-5-one as a yellow solid (4.98 g, 29%).

EI MS: m/e=244.1 ([M]$^+$).

Preparation of 2,8-difluoro-10,11-dihydro-dibenzo[a,d]cycloheptene-5-thione

The title compound was prepared in accordance with the general method of Example 1e from 2,8-difluoro-10,11-dihydro-dibenzo [a,d]cycloheptene-5-one. Blue solid.

EI MS: m/e=260.0 ([M]$^+$).

Preparation of 4-[(2',6,8'-trifluoro-10',11'-dihydrospiro[1,3-benzodioxole-2,5'-[5H]dibenzo[a,d]cyclohepten]-5-yl)carbonyl]-morpholine The title compound was prepared in accordance with the general method of Example 1f from (2-fluoro-4,5-dihydroxy-phenyl)-morpholin-4-yl-methanone (Example 1 d) and 2,8-difluoro-10,11-dihydro-dibenzo[a,d]cycloheptene-5-thione. Off-white foam.

EI MS: m/e=467.1 ([M]$^+$).

Example 6

Preparation of 4-[(2',6,8'-trifluoro-10',11'-dihydrospiro[1,3-benzodioxole-2,5'-[5H]dibenzo[a,d]cyclohepten]-5-yl)carbonyl]-piperidine The title compound was prepared in accordance with the general method of Example 1f from (2-fluoro-4,5-dihydroxy-phenyl)-piperidin-4-yl-methanone (Example 3b) and 2,8-difluoro-10,11-dihydro-dibenzo[a,d]cycloheptene-5-thione (Example 5b). Off-white foam.

ISP MS: m/e=466.4 ([M+H]$^+$).

Galenical Examples

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of formula (I)

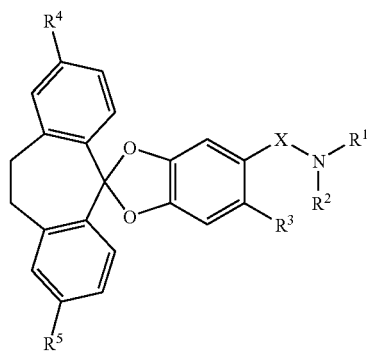

wherein
- $R^1$ and $R^2$ together with the nitrogen atom to which they are attached form a 4-, 5-, 6- or 7-membered monocyclic saturated heterocyclic ring which may optionally contain one or two further heteroatoms independently selected from O, N and S;
- $R^3$ is hydrogen, halogen, lower alkyl or cyano;
- $R^4$ and $R^5$ are each independently halogen; and
- X is —C(O)— or —SO$_2$—;

or a pharmaceutically acceptable salt thereof.

2. A compound according to claim 1, wherein $R^1$ and $R^2$ together with the nitrogen atom to which they are attached form a 6-membered monocyclic saturated heterocyclic ring which may optionally contain one further oxygen atom in the ring.

3. The compound according to claim 1, wherein $R^1$ and $R^2$ together with the nitrogen atom to which they are attached are selected from piperidinyl and morpholino.

4. The compound according to claim 1, wherein $R^3$ is hydrogen.

5. The compound according to claim 1, wherein $R^3$ is halogen.

6. The compound according to claim 1, wherein $R^4$ and $R^5$ are chloro.

7. The compound according to claim 1, wherein $R^4$ and $R^5$ are fluoro.

8. The compound according to claim 1, wherein X is —C(O)—.

9. The compound according to claim 1 which is:
4-[(2',8'-dichloro-6-fluoro-10',11'-dihydrospiro[1,3-benzodioxole-2,5'-[5H]dibenzo[a,d]cyclohepten]-5-yl)carbonyl]-morpholine,
and pharmaceutically acceptable salts thereof.

10. The compound according to claim 1 which is:
4-[(2',8'-dichloro-10',11'-dihydrospiro[1,3-benzodioxole-2,5'-[5H]dibenzo[a,d]cyclohepten]-5-yl)carbonyl]-piperidine,
and pharmaceutically acceptable salts thereof.

11. The compound according to claim 1 which is:
4-[(2',8'-dichloro-6-fluoro-10',11'-dihydrospiro[1,3-benzodioxole-2,5'-[5H]dibenzo[a,d]cyclohepten]-5-yl)carbonyl]-piperidine,
and pharmaceutically acceptable salts thereof.

12. The compound according to claim 1 which is:
4-[(2',8'-dichloro-6-fluoro-10',11'-dihydrospiro[1,3-benzodioxole-2,5'-[5H]dibenzo[a,d]cyclohepten]-5-yl)sulfonyl]-morpholine,
and pharmaceutically acceptable salts thereof.

13. The compound according to claim 1 which is:
4-[(2',6,8'-trifluoro-10',11'-dihydrospiro[1,3-benzodioxole-2,5'-[5H]dibenzo[a,d]cyclohepten]-5-yl)carbonyl]-morpholine,
and pharmaceutically acceptable salts thereof.

14. The compound according to claim 1 which is:
4-[(2',6,8'-trifluoro-10',11'-dihydrospiro[1,3-benzodioxole-2,5'-[5H]dibenzo[a,d]cyclohepten]-5-yl)carbonyl]-piperidine,
and pharmaceutically acceptable salts thereof.

15. A process for the manufacture of a compound of the formula

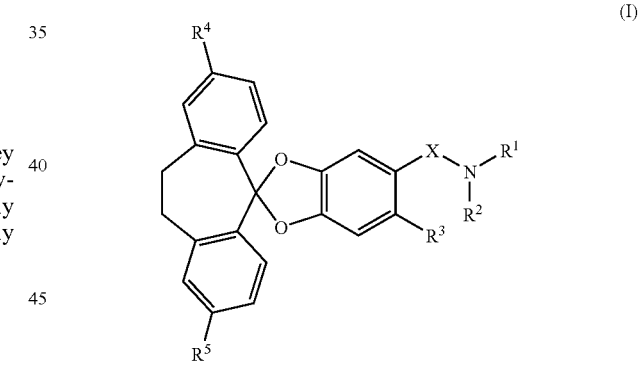

wherein
- $R^1$ and $R^2$ together with the nitrogen atom to which they are attached form a 4-, 5-, 6- or 7-membered monocyclic saturated heterocyclic ring which may optionally contain one or two further heteroatoms independently selected from O, N and S;
- $R^3$ is hydrogen, halogen, lower alkyl or cyano;
- $R^4$ and $R^5$ are each independently halogen; and
- X is —C(O)— or —SO$_2$—;

comprising: (a) ketalizing a compound of formula (A)

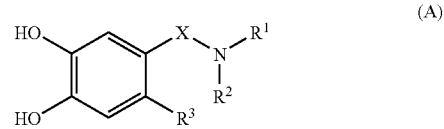

wherein $R^1$, $R^2$, $R^3$ and X are as defined in claim 1;

with a compound of formula (B)

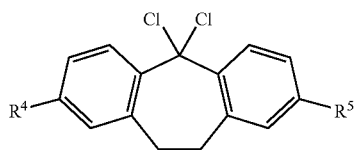

wherein $R^4$ and $R^5$ are as defined in claim 1; or (b) reacting a compound of formula (A)

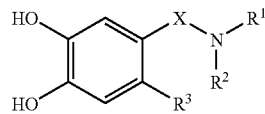

wherein $R^1$, $R^2$, $R^3$ and X are as defined in claim 1;
with a compound of formula (C)

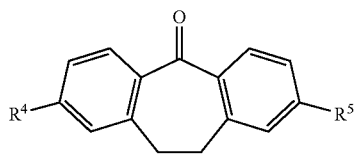

wherein $R^4$ and $R^5$ are as defined in claim 1; or (c) reacting a compound of formula (A)

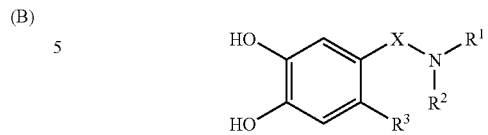

wherein $R^1$, $R^2$, $R^3$ and X are as defined in claim 1;
with a compound of formula (D)

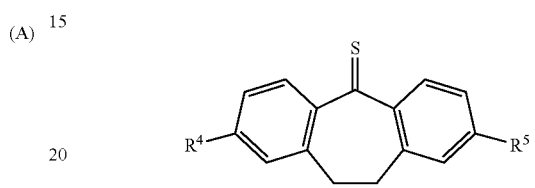

wherein $R^4$ and $R^5$ are as defined in claim 1.

16. A pharmaceutical compositions comprising a pharmacologically effective amount of a compound according to claim 1 and a pharmaceutically acceptable carrier and/or adjuvant.

17. A method for the treatment of obesity comprising administering a therapeutically effective amount of a composition according to claim 16 to a patient in need thereof.

* * * * *

UNITED STATES PATENT AND TRADEMARK OFFICE
CERTIFICATE OF CORRECTION

| | | |
|---|---|---|
| PATENT NO. | : 7,144,890 B2 | Page 1 of 1 |
| APPLICATION NO. | : 11/042884 | |
| DATED | : December 5, 2006 | |
| INVENTOR(S) | : Jean-Marc Plancher and Sven Taylor | |

It is certified that error appears in the above-identified patent and that said Letters Patent is hereby corrected as shown below:

Title page, item
(73) Assignee: Hoffman-La Roche Inc., Nutley, NJ (US)

should be

(73) Assignee: Hoffmann-La Roche Inc., Nutley, NJ (US)

Signed and Sealed this

Tenth Day of July, 2007

JON W. DUDAS
*Director of the United States Patent and Trademark Office*